United States Patent
Park et al.

(10) Patent No.: US 9,790,238 B2
(45) Date of Patent: Oct. 17, 2017

(54) STRONTIUM PRECURSOR, METHOD FOR PREPARING SAME, AND METHOD FOR FORMING THIN FILM BY USING SAME

(71) Applicant: Korea Research Institute of Chemical Technology, Daejeon (KR)

(72) Inventors: Bo-Keum Park, Gangwon-do (KR); Taek-Mo Chung, Daejeon (KR); Chang-Gyoun Kim, Daejeon (KR); Sheby Mary George, Daejeon (KR); Young-Kuk Lee, Daejeon (KR); Jong-Sun Lim, Daejeon (KR); Seog-Jong Jeong, Daejeon (KR); Dong-Ju Jeon, Daejeon (KR); Ki-Seok An, Daejeon (KR); Sun-Sook Lee, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 262 days.

(21) Appl. No.: 14/398,878

(22) PCT Filed: May 3, 2013

(86) PCT No.: PCT/KR2013/003866
§ 371 (c)(1),
(2) Date: Nov. 4, 2014

(87) PCT Pub. No.: WO2013/165212
PCT Pub. Date: Nov. 7, 2013

(65) Prior Publication Data
US 2015/0175629 A1 Jun. 25, 2015

(30) Foreign Application Priority Data

May 4, 2012 (KR) .................. 10-2012-0047439
May 4, 2012 (KR) .................. 10-2012-0047440

(51) Int. Cl.
*C07F 3/00* (2006.01)
*C23C 16/40* (2006.01)
(Continued)

(52) U.S. Cl.
CPC ............... *C07F 3/003* (2013.01); *C07F 3/00* (2013.01); *C23C 16/18* (2013.01); *C23C 16/409* (2013.01);
(Continued)

(58) Field of Classification Search
CPC .................................. C23C 16/18; C07F 3/00
See application file for complete search history.

(56) References Cited

U.S. PATENT DOCUMENTS

2002/0034586 A1* 3/2002 Leedham ............... C07F 7/006
427/255.36
2006/0178006 A1 8/2006 Xu et al.
(Continued)

FOREIGN PATENT DOCUMENTS

KR 10-2008-0113053 12/2008

OTHER PUBLICATIONS

Zhao et al. "Synthesis of thin films of barium titanate and barium strontium titanate nanotubes on titanium substrates," Materials Letters, 4 pages, Feb. 2005.
(Continued)

*Primary Examiner* — Elizabeth Burkhart
(74) *Attorney, Agent, or Firm* — Baker & Hostetler LLP

(57) ABSTRACT

Disclosed herein is a novel strontium precursor containing a beta-diketonate compound. Being superior in thermal stability and volatility, the strontium precursor can form a quality strontium thin film.

5 Claims, 4 Drawing Sheets

(51) Int. Cl.
*C23C 16/18* (2006.01)
*C23C 16/44* (2006.01)
*C23C 16/455* (2006.01)

(52) U.S. Cl.
CPC ........ *C23C 16/44* (2013.01); *C23C 16/45525* (2013.01)

(56) References Cited

U.S. PATENT DOCUMENTS

| | | | |
|---|---|---|---|
| 2008/0085365 A1* | 4/2008 | Yamada | C07C 215/08 427/255.28 |
| 2008/0171890 A1* | 7/2008 | Kim | C07C 215/08 556/146 |
| 2008/0194088 A1 | 8/2008 | Srinivasan et al. | |
| 2010/0034719 A1 | 2/2010 | Dussarrat et al. | |
| 2010/0095865 A1 | 4/2010 | Xu et al. | |
| 2010/0291299 A1 | 11/2010 | Cameron et al. | |
| 2011/0212629 A1* | 9/2011 | Ivanov | C09D 1/00 438/778 |

OTHER PUBLICATIONS

Mao et al., "Large-Scale Synthesis of Single-Crystalline Perovskite Nanostructures," J. Am. Chem. Soc, 2 pages Aug. 2003.

Gong et al., "Titanium oxide nanotube arrays prepared by anodic oxidation," J. Matter Res., 4 pages, Sep. 2001.

Padture et al., Hydrothermal Synthesis of Thin Films of Barium Titanate Ceramic Nano-Tubes at 200° C., J. Am. Ceram. Soc., 3 pages, Jul. 2003.

Phule et al., "review Low-temperature synthesis and processing of electronic materials in the BaO—TiO2 system," Journal of Materials Science, 15 pages, 1990.

Hill et al., "Why are there so Few Magnetic Ferroelectrics?," J. Phys. Chem. B, 16 Pages, Apr. 2000.

Asaoka et al., "Heteroepitaxial growth of SrO on hydrogen-terminated Si(100) surface," Thin Solid Films, 4 pages, 2000.

Okamoto et al. "Blue emitting Sr 2 Ga 2 S 5: Ce phosphor thin films grown by multisource deposition," Applied Physics Letters, 4 pages, Feb. 2000.

Tanaka et al., "Blue luminescent SrGa,S, : Ce thin films grown by molecular beam epitaxy," Journal of Crystal Growth, 4 pages, 1995.

Paw et al., Low-Melting, mononuclear Tetahydrofuran Complexes of M (2,2,6,6-teramethyleheptane-3,5-dionate)2 (M=Ba,Sr) and Related Analogues, Inorg. Chem., 4 pages, Apr. 2000.

Mizushima et al., "Preparation of YBa2CU07-d thin film by laser-assisted metal-organic chemical vapor deposition using highly volatile fluorocarbon-based Ba source," Journal of Materials Research, 5 pages, Apr. 1996.

Shamlian et al., "Metal-Organic Chemical Vapour Deposition of YBCO using a New, Stable and Volatile Barium Precursor," J. Mater. Chem. 5 pages, Jan. 1994.

Gardiner et al. "Volatile Barium B-Diketonate Polyether Adducts. Synthesis, Characterization, and Metalloorganic Chemical Vapor Deposition", 7 pages, Aug. 1991.

* cited by examiner

STRONTIUM PRECURSOR, METHOD FOR PREPARING SAME, AND METHOD FOR FORMING THIN FILM BY USING SAME

CROSS-REFERENCE TO RELATED APPLICATIONS

This application is the National Stage of International Application No. PCT/KR2013/003866, filed May 3, 2013, which claims the benefit of and priority to Korean application No. 10-2012-0047440, filed May 4, 2012 and Korean application No. 10-2012-0047439, filed May 4, 2012, the entireties of which applications are incorporated herein by reference for any and all purposes.

TECHNICAL FIELD

The present invention relates to a novel strontium precursor. More particularly, the present invention relates a strontium precursor that exhibits excellent thermal stability and volatility and thus can be applied in the formation of a quality strontium-containing thin film even at a low temperature, a preparing method thereof, and a method for forming a strontium-containing thin film, using the same.

BACKGROUND ART

Strontium compounds are used in oxygen-ionic and electronic conductive thin films when being in the form of $SrTiO_3$, $SrBi_2Ta_2O_9$, $Ba_xSr_{1-x}TiO_3$, LaSrCoFe, and are found in thin film electroluminescent displays when being in the form of $SrGa_2S_4$:Ce. Like this, strontium compounds are used as precursors for preparing strontium-containing heterogeneous metal thin films, nano-size strontium oxides, and strontium-containing heterogeneous metal particles.

In addition, strontium titanate ($SrTiO_3$) and barium strontium titanate (($Ba, Sr$)$TiO_3$), both being alkaline earth metal-containing oxides with a Perovskite structure, find applications in various fields including nonvolatile ferroelectric memory, microwave devices, dynamic random access memory (DRAMs), multilayer capacitors, electro optical devices, actuators, transducers, high-k dielectrics, and micro-electromechanical systems (MEMs) (Zhao, J.; Wang, X.; Chen, R.; Li. L. Materials Letters 2005, 59, 2329; Mao, Y.; Baneriee, S.; Wong, S. S. J. Am. Chem. Soc. 2003, 125, 15718; Gong, D.; Grimes, C. A.; Varghese, O. K; Hu, W.; Singh, R. S.; Chen, Z.; Dickey, D. J. J. Mater. Res. 2001, 16, 3331; Padture, N. P. Wei, X. Z. J. Am. Ceram. Soc. 2003, 86, 2215; Phule, P. P.; Risbud, S. H. J. Mater. Sci. 1990, 25, 1169; Hill, N. A. J. Phys. Chem. B 2000, 104, 6694). Further, SrO is known to act as a buffer layer between Si and $SrTiO_3$, and alkaline earth thiogallates such as $SrGa_2S_4$:Ce are studied for use in phosphor thin films of electroluminescent displays (Asaoka, H.; Saiki, K.; Koma, A.; Yamamoto, H. Thin Solid Films 2000, 369, 273; Okamoto, S.; Tanaka, K.; Inoue, Y. Appl. Phys. Lett. 2000, 76, 946; Tanaka, K.; Inoue, Y.; Okamoto, S.; Kobayashi, K. J. Cryst. Growth 1995, 150, 1211).

To prepare the above-mentioned materials, various methods such as sol-gel, MOD (metal-organic decomposition), PLD (pulsed laser ablation), CVD (chemical vapor deposition), MOCVD (metal-organic chemical vapor deposition), ALD (atomic layer deposition), etc. have been employed. For use in these methods, various precursors are known, including alkoxides, aryloxides, b-diketonates, metallocenes, bis(trimethylsilyl)amide, and alkylamide. However, most of these precursors are dimers or higher oligomers with high volatile temperatures. In order to improve their volatility, the precursors are fluorinated, which leads contamination of the thin films with fluorides (Paw, W.; Baum, T. H.; Lam, K.-C.; Rheingold, A. L. Inorg. Chem. 2000, 39, 2011; Mizushima, Y.; Hirabayashi, I. J. Mater. Res. 1996, 11, 2698; Shamlian, S. H.; Hitchman, M. L.; Cook, S. L.; Richards. B. C. J. Mater Chem. 1994, 4, 81; Gardiner, R. A.; Brown, D. W.; Kirlin, P. S.; Rheingold, A. L. Chem. mater. 1991, 3, 1053). Meanwhile, Korean Patent Application Unexamined Publication No. 2008-0113053 discloses a strontium precursor containing a ligand composed only of cyclopentadienyl, but this precursor cannot be a solution to the problems mentioned above.

DISCLOSURE

Technical Problem

Accordingly, the present invention has been made keeping in mind the above problems occurring in the prior art, and an object of the present invention is to provide a novel strontium precursor that exhibits high thermal stability and volatility and which can be readily applied at a low temperature for the formation of a quality thin film.

Technical Solution

In order to accomplish the object, the present invention provides a strontium precursor represented by the following Chemical Formula 1:

[Chemical Formula 1]

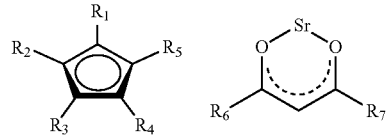

wherein, R1, R2, R3, R4, and R5 are independently H, or linear or branched alkyl of C1-C10; and R6 and R7 are independently linear or branched alkyl of C1-C10, or fluorinated alkyl of C1-C10.

In addition, the present invention provides a method for preparing a strontium precursor represented by Chemical Formula 1, comprising: a) reacting a compound represented by the following Chemical Formula 2 with $SrI_2$ to synthesize a compound represented by the following Chemical Formula 3; and b) reacting the compound of Chemical Formula 3 with a compound represented by the following Chemical Formula 4:

[Chemical Formula 2]

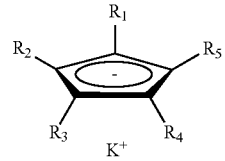

wherein, R1, R2, R3, R4, and R5 are independently H, or linear or branched alkyl of C1-C10.

[Chemical Formula 3]

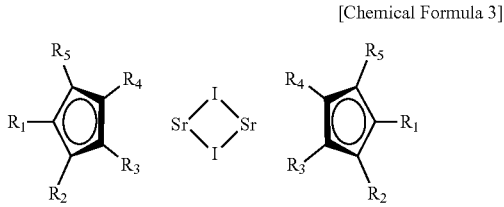

wherein, R1, R2, R3, R4, and R5 are independently H, or linear or branched alkyl of C1-C10.

[Chemical Formula 4]

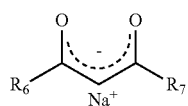

Wherein, R6 and R7 are independently H, or linear or branched alkyl of C1-C10, or fluorinated alkyl of C1-C10.

Also, the present invention provides a strontium precursor represented by the following Chemical Formula 5:

[Chemical Formula 5]

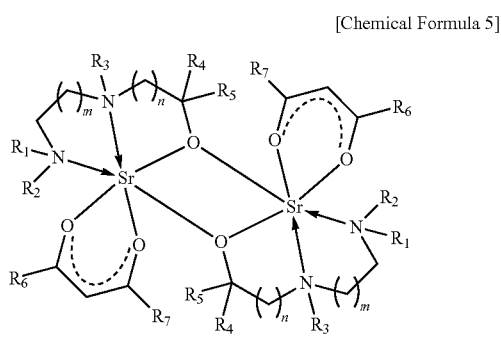

wherein, R1, R2, and R3 are independently H, or linear or branched alkyl of C1-C10; R4, R5, R6, and R7 are independently H, or linear or branched alkyl of C1-C10, or fluorinated alkyl of C1-C10; m and n are independently an integer of 1 to 3.

Further, the present invention provides a method for preparing a strontium precursor represented by Chemical Formula 5, comprising: a) reacting a compound represented by the following Chemical Formula 6 with $Sr(NR_8R_9)_2$ to synthesize a compound represented by the following Chemical Formula 7; and b) reacting the compound of Chemical Formula 7 with a compound represented by the following Chemical Formula 8.

[Chemical Formula 6]

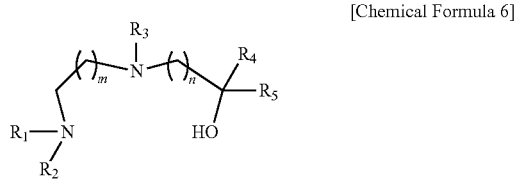

wherein, R1, R2, and R3 are independently H, or linear or branched alkyl of C1-C10; and R4 and R5 are independently H, or linear or branched alkyl of C1-C10, or fluorinated alkyl of C1-C10; and m and n are independently an integer of 1 to 3.

[Chemical Formula 7]

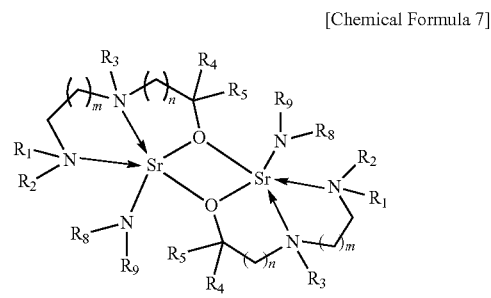

wherein, R1, R2, and R3 are independently H, or linear or branched alkyl of C1-C10, R4 and R5 are independently H, or linear or branched alkyl of C1-C10, or fluorinated alkyl of C1-C10, R8 and R9 are independently H, or linear or branched alkyl of C1-C10, or trialkylsilyl ($—SiR_3$); and m and n are independently an integer of 1 to 3.

[Chemical Formula 8]

wherein, R6 and R7 are independently H, or linear or branched alkyl of C1-C10, or fluorinated alkyl of C1-C10.

Further, the present invention provides a method for growing a strontium-containing thin film using the strontium precursor of Chemical Formula 1 or 5.

Advantageous Effects

Being superior in thermal stability and volatility, the strontium precursor represented by Chemical Formula 1 or 5 can be readily applied in the formation of quality strontium-containing thin films.

BEST MODE

Figure 1:
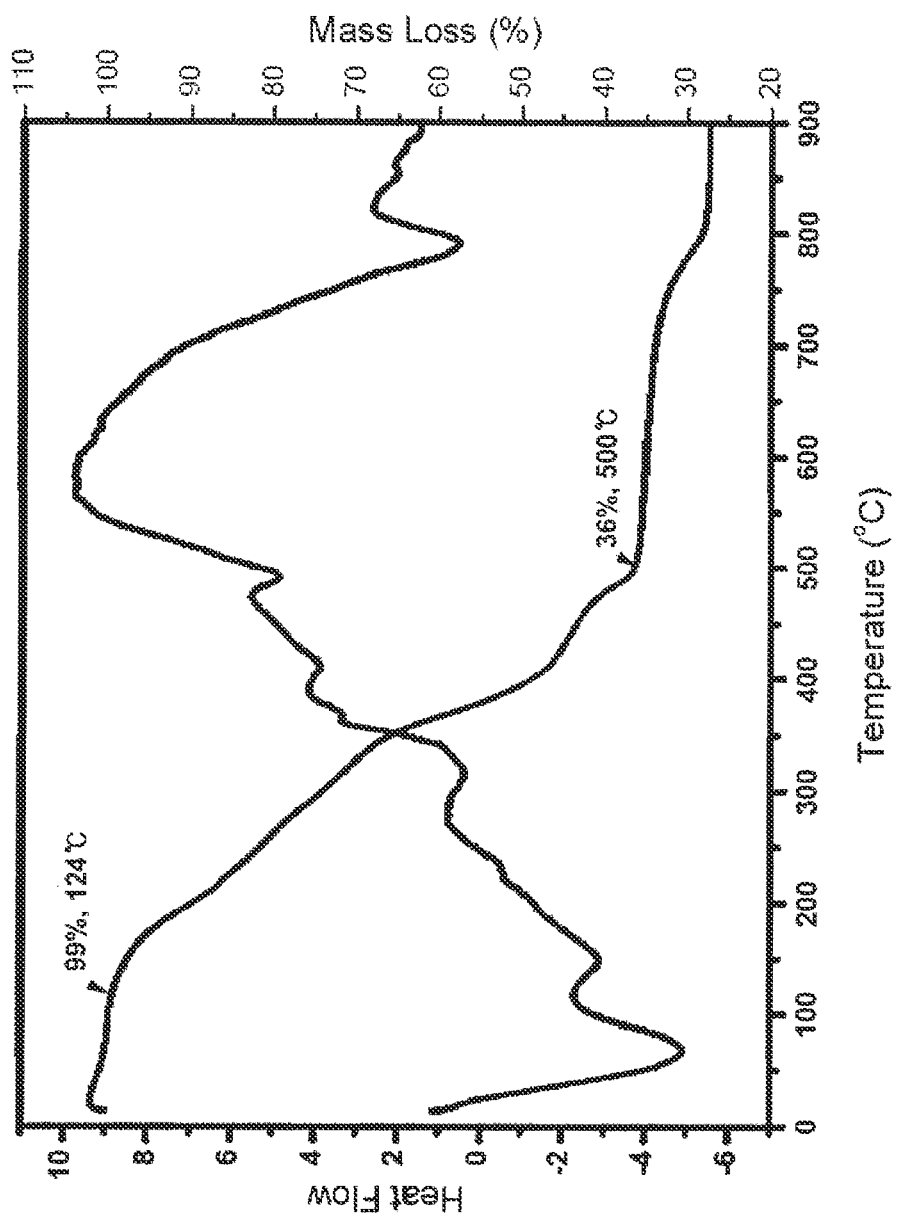
FIG. 1 shows TG data of $Sr(^{3iPr}Cp)(tmhd)$.

In accordance with an aspect thereof, the present invention addresses a strontium precursor represented by the following Chemical Formula 1:

[Chemical Formula 1]

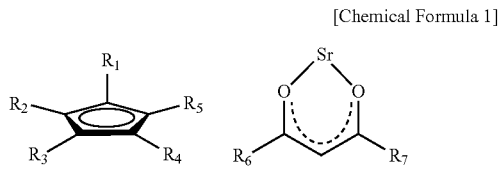

wherein, R1, R2, R3, R4 and R5 are independently H, or linear or branched alkyl of C1-C10; and R6 and R7 are independently H, or linear or branched alkyl of C1-C10, or linear or branched fluorinated alkyl of C1-C10.

The strontium precursor represented by Chemical Formula 1 in accordance with the present invention may be expressed as the general formula Sr(Cp')(bdk). The preparation of this compound may start with the reaction of a cyclopentadiene compound represented by the following Chemical Formula 2 with SrI$_2$ in an organic solvent, followed by allowing the resulting cyclopentadiene strontium represented by the following Chemical Formula 3 to undergo a substitution reaction with a beta-diketonate represented by the following Chemical Formula 4 in an organic solvent:

[Chemical Formula 2]

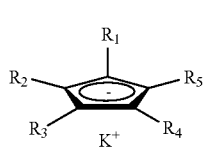

wherein, R1, R2, R3, R4 and R5 are independently H, or linear or branched alkyl of C1-C10.

[Chemical Formula 3]

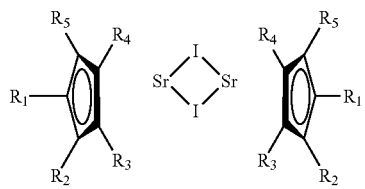

wherein, R1, R2, R3, R4 and R5 are independently H, or linear or branched alkyl of C1-C10.

[Chemical Formula 4]

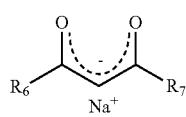

wherein, R6 and R7 are independently H, or linear or branched alkyl of C1-C10, or linear or branched fluorinated alkyl of C1-C10.

Examples of the solvent useful for the reactions include toluene, tetrahydrofuran, hexane, and diethylether, with preference for toluene.

Reaction procedures of preparing the strontium precursor of the present invention may be as shown in the following Reaction Schemes 1 and 2.

[Reaction Scheme 1]

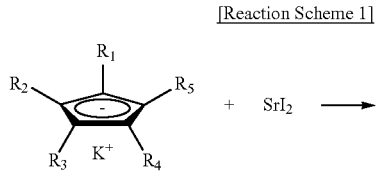

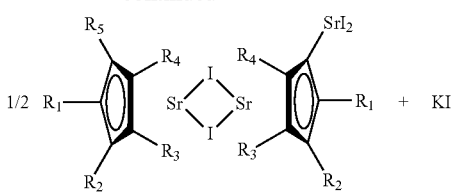

wherein, R1, R2, R3, R4, and R5 are independently H, or linear or branched alkyl of C1-C10.

As shown in Reaction Scheme 1, a substitution reaction is carried out at room temperature for 12 hrs to 24 hrs in a solvent such as toluene, tetrahydrofuran, hexane, or diethylether to give Sr'CpI as a yellow solid.

[Reaction Scheme 2]

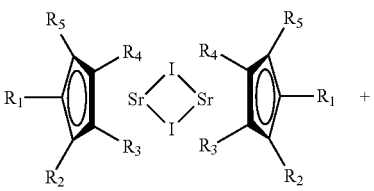

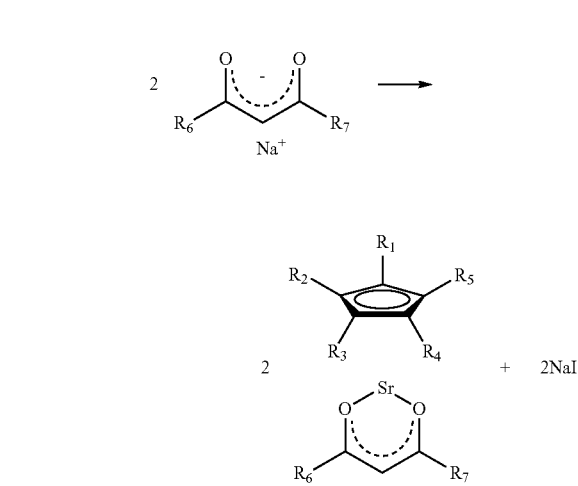

wherein, R1, R2, R3, R4, and R5 are independently H, or linear or branched alkyl of C1-C10; and R6 and R7 are independently H, or linear or branched alkyl of C1-C10, or linear or branched fluorinated alkyl of C1-C10.

Next, as illustrated in Reaction Scheme 2, the resulting compound Sr'CpI of Reaction Scheme 1 is allowed to undergo a substitution reaction with compound 3 in a solvent, such as toluene, tetrahydrofuran, hexane, or diethylether, at room temperature for 12 to 24 hrs. After filtration at a reduced pressure, the filtrate is dried in a vacuum to afford the novel strontium precursor as a dark yellow solid. During the procedures of Reaction Schemes 1 and 2, by-products may be produced. They may be removed by sublimation or recrystallization to give the novel strontium precursor of high purity.

In addition, the present invention addresses a strontium precursor represented by the following Chemical Formula 5:

[Chemical Formula 5]

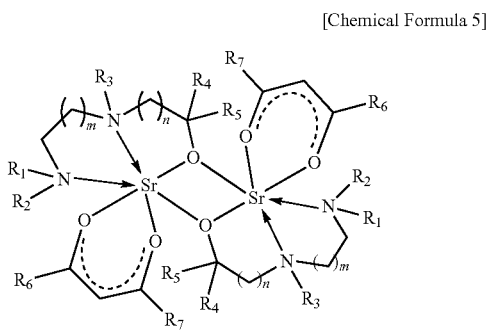

wherein, R1, R2 and R3 are independently H, or linear or branched alkyl of C1-C10; R4, R5, R6, and R7 are independently H, or linear or branched alkyl of C1-C10, or linear or branched fluorinated alkyl of C1-C10; and m and n are independently an integer of 1 to 3.

Also, the present invention is concerned with a strontium precursor represented by the following Chemical Formula 7.

[Chemical Formula 7]

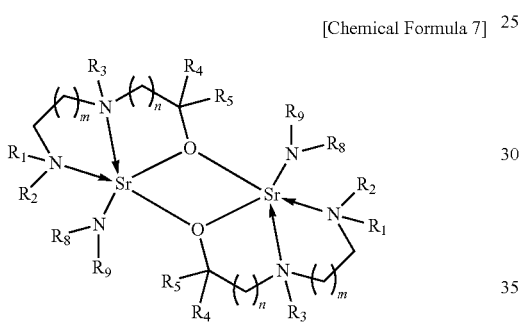

wherein, R1, R2 and R3 are independently H, or linear or branched alkyl of C1-C10; R4 and R5 are independently H, or linear or branched alkyl of C1-C10, or linear or branched fluorinated alkyl of C1-C10; R8 and R9 are independently H, or linear or branched alkyl of C1-C10, or trialkylsilyl (—$SiR_3$); and m and n are independently an integer of 1 to 3.

The strontium precursor, represented by Chemical Formula 5, according to the present invention can be prepared by reacting a compound represented by the following Chemical Formula 6 as a starting material with $Sr(NR8R9)_2$ in an organic solvent to synthesize a strontium compound represented by Chemical Formula 7, and then subjecting the strontium compound of Chemical Formula 7 to substitution reaction with a beta-diketonate represented by the following Chemical Formula 8.

[Chemical Formula 6]

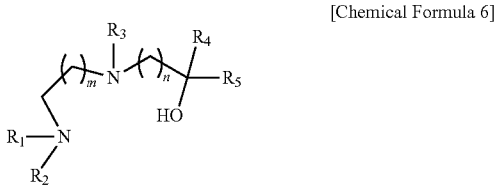

wherein, R1, R2 and R3 are independently H, or linear or branched alkyl of C1-C10; R4 and R5 are independently H or linear or branched alkyl of C1-C10, or linear or branched fluorinated alkyl of C1-C10; and m and n are independently an integer of 1 to 3.

[Chemical Formula 8]

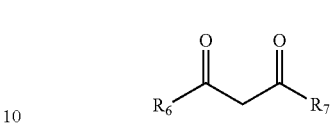

(R6 and R7 are independently H or linear or branched alkyl of C1-C10, or linear or branched fluorinated alkyl of C1-C10.)

Examples of the solvent useful in the reactions include toluene, tetrahydrofuran, hexane, and diethylether, with preference for toluene.

Preparation of a strontium precursor according to the present invention may be as illustrated in the following Reaction Scheme 3.

[Reaction Scheme 3]

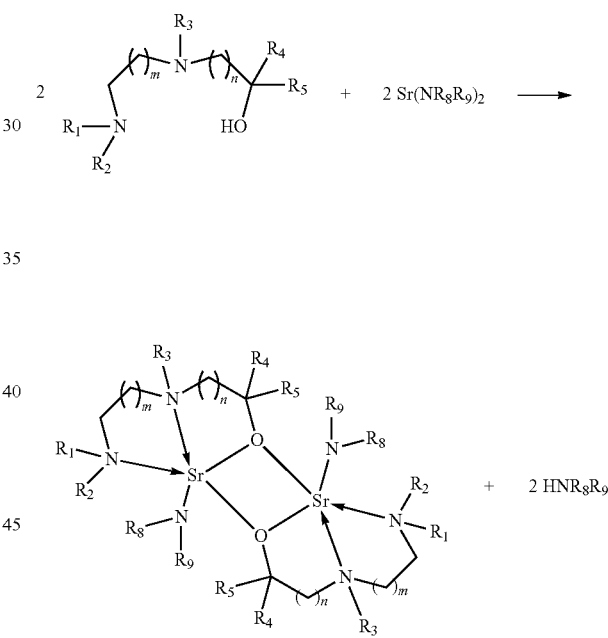

wherein, R1, R2 and R3 are independently H, or linear or branched alkyl of C1-C10; R4 and R5 are independently H, linear or branched alkyl of C1-C10, or linear or branched fluorinated alkyl of C1-C10; and R8 and R9 are independently H, linear or branched alkyl of C1-C10, or trialkylsilyl (—$SiR_3$); and m and n are independently an integer of 1 to 3.

As shown in Reaction Scheme 3, a substitution reaction is carried out at room temperature for 12 to 24 hrs in a solvent such as tetrahydrofuran, hexane, or diethylether to give an intermediate [Sr(aminoalkoxide)(amide)]$_2$ (1) as a white solid.

Another reaction procedure of preparing a strontium precursor according to the present invention may be as illustrated in the following Reaction Scheme 4.

[Reaction Scheme 4]

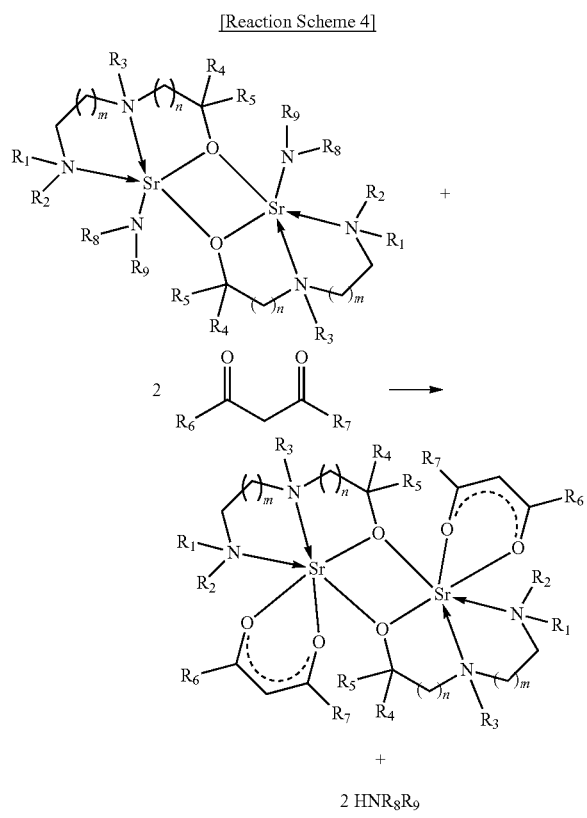

wherein, R1, R2 and R3 are independently H, or linear or branched alkyl of C1-C10; R4, R5, R6, and R7 are independently H, linear or branched alkyl of C1-C10, or linear or branched fluorinated alkyl of C1-C10; and R8 and R9 are independently H, linear or branched alkyl of C1-C10, or trialkylsilyl (—SiR$_3$); and m and n are independently an integer of 1 to 3.

As illustrated in Reaction Scheme 4, the resulting compound Sr(aminoalkoxide)(amide) (1) of Reaction Scheme 3 is allowed to undergo a substitution reaction with tetramethyl heptane dione in a solvent, such as toluene, tetrahydrofuran, hexane, or diethylether, at room temperature for 12 to 24 hrs. After filtration at a reduced pressure, the filtrate is dried in a vacuum to afford the novel strontium precursor as a white crystalline solid. During the procedures of Reaction Schemes 3 and 4, by-products may be produced. They may be removed by sublimation or recrystallization to give the novel strontium precursor of high purity.

In these reactions, the reactants are used at stoichiometric ratios.

The novel strontium precursor represented by Chemical Formula 1 or 5 takes the form of a white solid at room temperature, and is thermally stable and highly volatile.

As a precursor for use in thin films, the novel strontium precursor of the present invention can be applied to chemical vapor deposition or atomic layer deposition both of which are widely used for the preparation of STO or BST.

A better understanding of the present invention may be obtained through the following examples that are set forth to illustrate, but are not to be construed as limiting the present invention.

Mode for Invention

Synthesis of Strontium Precursor

Example 1: Preparation of Sr($^{3iPr}$Cp)(tmhd)

In a 200 mL Schlenk flask, a solution of strontium iodide (0.4 g, 1.2 mmol, 1 eq) in THF (100 mL) was mixed with 2,3,5-triisopropyl cyclopentadiene potassium (0.27 g, 1.2 mmol, 1 eq) in THF (50 mL) while stirring for 24 hrs. After removing potassium iodide by filtration, the filtrate was reacted with 2,2,6,6-tetramethyl heptanedione sodium (0.25 g, 1.2 mmol) in THF (50 mL) while stirring for an additional 24 hrs. Distillation in a vacuum was carried out to dryness to afford the compound as a yellow solid: Yield 52%.

The compound Sr($^{3iPr}$Cp)(tmhd) was analyzed for $^1$H-NMR (THF-d8), $^1$H-NMR (C$_6$D$_6$), and FT-IR, as follows.

NMR data: ($^1$H, THF-d8) δ 1.07 (s, 18H), 1.03-1.1 (several singlets, 18H), 2.8 (m, 3H), 5.4 (s, 1H), 6.02 (s, 1H).

NMR data: ($^1$H, C$_6$D$_6$) δ 1.05-1.4 (several singlets, 18H), 1.24 (s, 18H), 2.8 (m, 3H), 5.9 (s, 1H), 6.2 (s, 1H). ($^{13}$C, C$_6$D$_6$) δ 22.9, 23.2, 26.3, 27.0, 28.9, 29.0, 30.2, 39.1, 41.6, 91.5, 124.02, 141.6, 143.9, 152.3, 201.6.

FT-IR (cm$^{-1}$): 2960 (s), 2868 (m), 1580 (s), 1537 (w), 1500 (s), 1410 (s), 1357 (m), 1130 (w), 866 (w), 814 (w), 472 (w).

Example 2: Preparation of Sr($^{2t-But}$Cp)(tmhd)

In a 200 mL Schlenk flask, a solution of strontium (0.4 g, 1.2 mmol, 1 eq) in THF (100 mL) was mixed with a solution of 1,3-di-t-butyl cyclopentadiene potassium (0.26 g, 1.2 mmol, 1 eq) in THF (50 mL) while stirring for 24 hrs. After removing potassium iodide by filtration, the filtrate was reacted with 2,2,6,6-tetramethyl heptanedione sodium (0.25 g, 1.2 mmol) in THF (50 mL) while stirring for an additional 24 hrs. Vaporization was carried out in a vacuum to dryness to afford the compound as a yellow solid: Yield 56%.

The compound Sr($^{2t-But}$Cp)(tmhd) was analyzed for $^1$H-NMR (C$_6$D$_6$), and FT-IR, as follows.

NMR data: ($^1$H, C$_6$D$_6$) δ 1.13-1.32 (several singlets, 18H), 1.23 (s, 18H), 5.9 (s, 1H), 6.4 (singlets, 2H).

FT-IR (cm$^{-1}$): 2960 (s), 2867 (m), 1598 (s), 1580 (s), 1500 (s), 1420 (s), 1360 (s), 1130 (w), 866 (w), 793 (w), 476 (w).

Example 3: Preparation of Sr(demamp)(btsa) (1)

In a Schlenk flask, a solution of 1-((2-(dimethylamino) ethyl)(methyl)amino)-2-methylpropan-2-ol (demampH) (0.17 g, 1 mmol) in 15 mL of toluene was dropwise added to a solution of Sr(btsa)$_2$.2DME (0.59 g, 1 mmol, 1 eq) in 15 mL of toluene. After stirring at room temperature for 15 hrs, the resulting reaction mixture was filtered, and the toluene was removed by distillation to dryness to afford the compound as a white solid (0.4 g, yield 95%). During quenching, X-ray crystals grew in the concentrated toluene.

The compound Sr(demamp)(btsa)(1) was analyzed for $^1$H-NMR and FT-IR, as follows.

$^1$H NMR ($C_6D_6$, 300 MHz): δ 0.38 (s, 18H), 1.23 (s, 3H), 1.46 (s, 3H), 1.54 (m, 1H), 1.68 (m, 1H), 2.00 (m, 1H), 2.07 (s, br, 6H), 2.11 (d, 1H), 2.15 (s, 3H), 2.33 (d, 1H), 2.65 (m, 1H).

FTIR: ($cm^{-1}$) 2945 (s), 2837 (w), 1484 (w), 1244 (w), 1059 (s), 961 (w), 883 (w), 817 (m), 659 (w).

Anal. Calcd for $C_{30}H_{78}N_6O_2Si_4Sr_2$: C, 42.76; H, 9.33; N, 9.97.

Found: C, 41.92; H, 9.15; N, 9.54.

Example 4: Preparation of Sr(demamp)(tmhd)(2)

In a Schlenk flask, a solution of tetramethylheptanedione (tmhd) (0.19 g, 1 mmol) in 5 mL of toluene was dropwise added to a solution of Sr(demamp)(btsa)(1) (0.84 g, 1 mmol) in 5 mL of toluene at room temperature, and then stirred for 12 hrs. After completion of the reaction, toluene was distilled, and the residue was dissolved in hexane, and filtered to give the compound as a white solid (0.41 g, Yield 93%). During quenching, X-ray crystals grew in the concentrated solution.

The resulting compound Sr(demamp)(tmhd)(2) was analyzed for $^1$H-NMR and FT-IR as follows.

$^1$H NMR ($C_6D_6$, 300 MHz): δ 1.21 (s, br), 1.34 (s, 18H), 1.41 (s, br), 2.08 (s), 2.14 (s), 2.44 (s, br), 5.87 (s, 1H).

FTIR: ($cm^{-1}$) 2950 (s), 2863 (m), 1589 (s), 1534 (w), 1504 (m), 1450 (s), 1423 (s), 1355 (m), 1225 (w), 1198 (w), 1185 (w), 864 (w), 470 (w).

Anal. Calcd for $C_{40}H_{80}N_4O_6Sr_2$: C, 54.08; H, 9.08; N, 6.31.

Found: C, 53.71; H, 9.35; N, 6.01.

Analysis of Strontium Precursors

Figure 2:
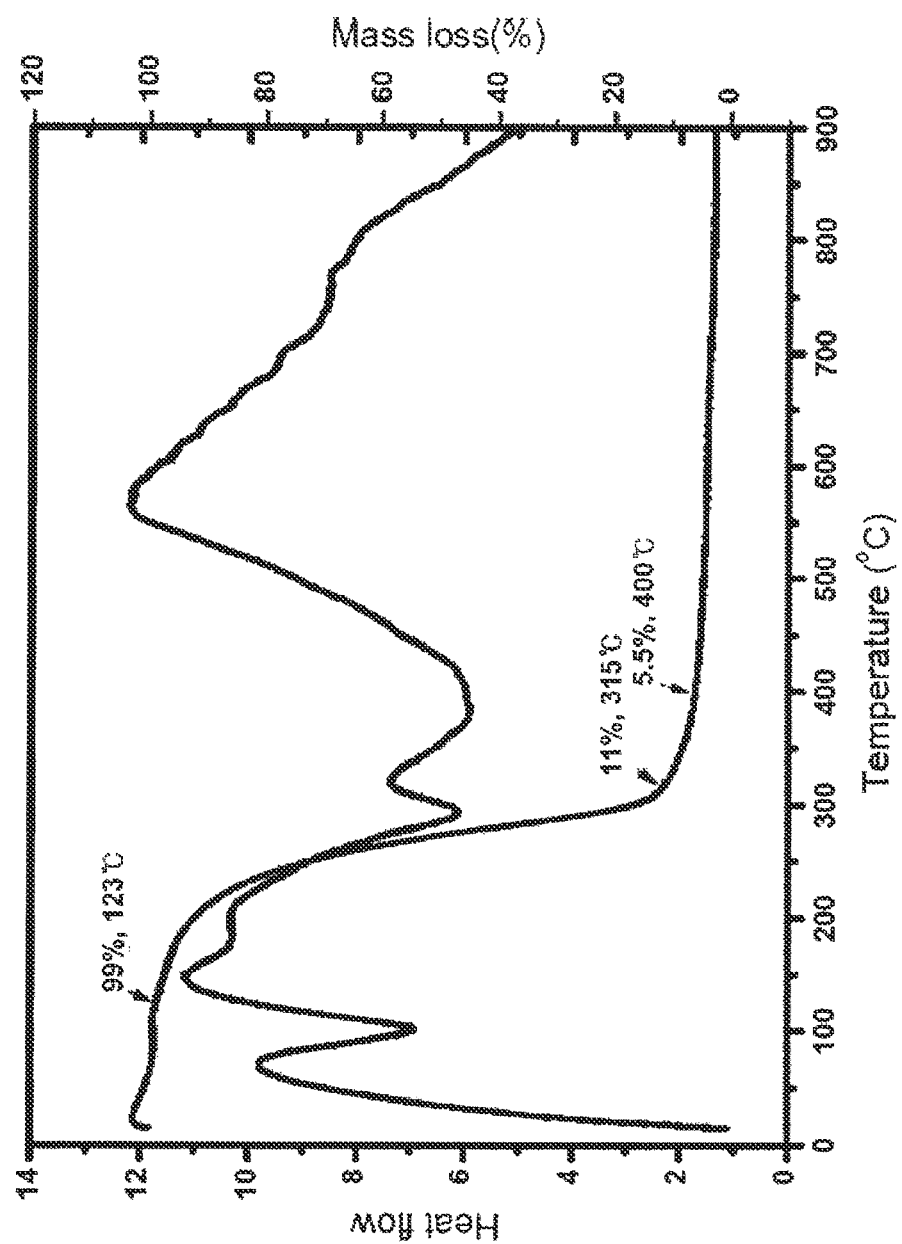
FIG. 2 shows TG data of $Sr(^{2t-Bu}Cp)(tmhd)$.

Sr($^{3iPr}$Cp)(tmhd) of Example 1 and Sr($^{2t-But}$Cp)(tmhd) of Example 2 were measured for thermal stability, volatility, and degradation temperature by a thermogravimetric analysis (TGA) method. In the TGA method, the products were heated at a rate of 10° C./min to 900° C. while argon gas was introduced at a pressure of 1.5 bar/min. TGA graphs of the strontium precursor compounds synthesized in Examples 1 and 2 are given in FIGS. 1 and 2, respectively. As shown in FIG. 1, the strontium precursor compound obtained in Example 1 started to degrade at around 124° C., with a total of mass loss by 64% or higher at 500° C. As can be seen in FIG. 2, the strontium precursor compound obtained in Example 2 started to undergo mass loss at around 123° C. with a total of mass loss of 89% or higher at 315° C.

Figure 3:
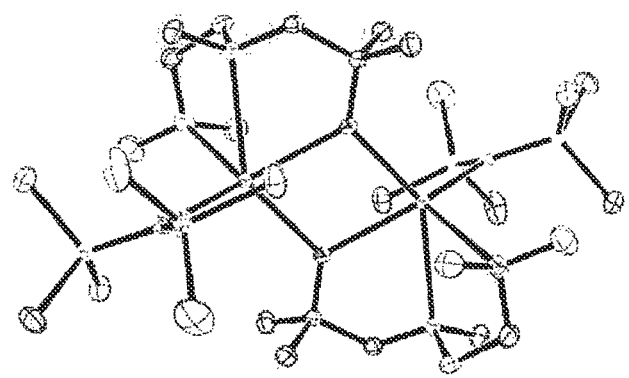
FIG. 3 depicts a structure of Sr(demamp)(btsa), as determined by X-ray crystallography.
Figure 4:
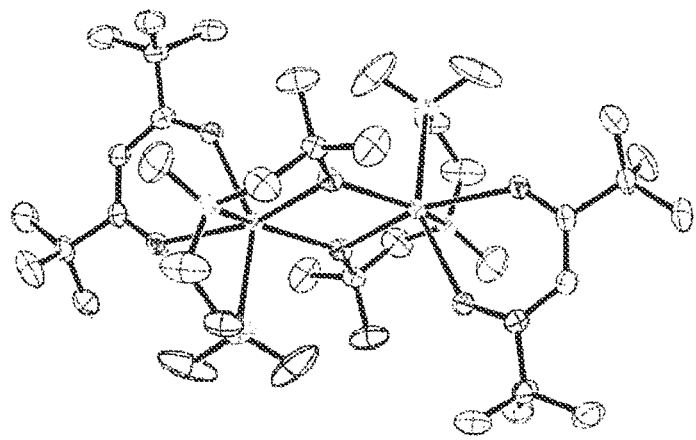
FIG. 4 depicts a structure of Sr(demamp)(tmhd), as determined by X-ray crystallography.

Structural examination was made on the strontium precursor compounds synthesized in Examples 3 and 4, using Bruker SMART APEX II X-ray Diffractometer, and their X-ray structures are depicted in FIGS. 3 and 4, respectively. As can be seen, concrete structures of Sr(demamp)(btsa)(1) and Sr(demamp)(tmhd)(2) could be obtained.

Figure 5:
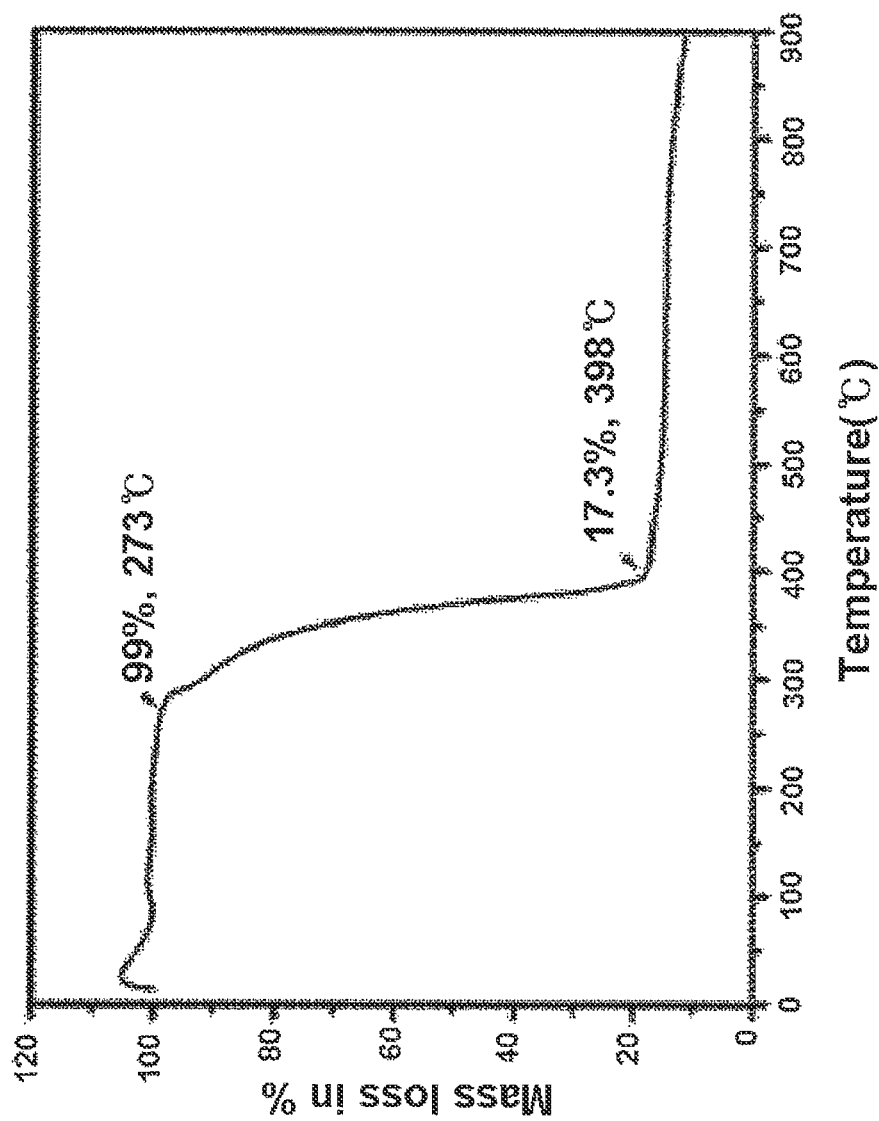
FIG. 5 shows TG data of Sr(demamp)(tmhd).

Also, a Thermo Gravimetric Analysis (TGA) method was used to examine the thermal stability, volatility, and degradation temperature of Sr(demamp)(tmhd)(2). In the TGA method, the product was heated at a rate of 10° C./min to 900° C. while argon gas was introduced at a pressure of 1.5 bar/min. FIG. 5 is a TGA graph of the strontium precursor compound synthesized in Example 4. As can be seen in FIG. 9, the strontium precursor compound obtained in Example 4 was observed to start degradation at 273° C., with a total of mass loss of 83% at 398° C.

What is claimed is:

1. A strontium precursor, represented by the following Chemical Formula 5:

[Chemical Formula 5]

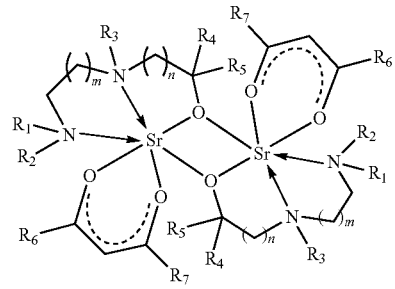

wherein,

R1, R2, R3, R4, and R5 are independently methyl group ($—CH_3$);

R6 and R7 are independently tertiary-butyl group ($—C(CH_3)_3$); and m and n are independently 1.

2. A method for preparing strontium precursor represented by Chemical Formula 5 of claim 1, using an amino alcohol represented by the following Chemical Formula 6:

[Chemical Formula 6]

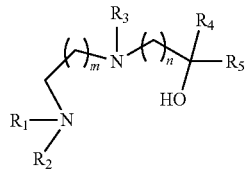

wherein,

R1, R2, R3, R4, and R5 are independently methyl group ($—CH_3$); and m and n are independently 1.

3. The method of claim 2, wherein the method comprises:

a) reacting a compound represented by the following Chemical Formula 6 with $Sr(NR_8R_9)_2$ to synthesize a compound represented by the following Chemical Formula 7; and b) reacting the compound of Chemical Formula 7 with a compound represented by the following Chemical Formula 8:

[Chemical Formula 6]

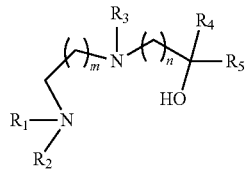

wherein,

R1, R2, R3, R4, and R5 are independently methyl group ($—CH_3$); and m and n are independently 1;

[Chemical Formula 7]

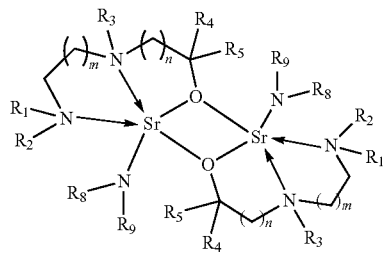

wherein,
R1, R2, R3, R4, and R5 are independently methyl group (—CH$_3$);
R8 and R9 are independently H, linear or branched alkyl of C1-C10, or trialkylsilyl (—SiR$_3$); and
m and n are independently 1;

[Chemical Formula 8]

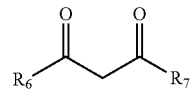

wherein,
R6 and R7 are independently tertiary-butyl group (—C(CH$_3$)$_3$).

4. A method for growth of a strontium-containing thin film, using the strontium precursor of claim 1.

5. The method of claim 4, wherein the growth of the strontium-containing thin film is carried out by chemical vapor deposition (CVD) or atomic layer deposition (ALD).

* * * * *